(12) United States Patent
Luo (10) Patent No.: US 11,527,724 B2
(45) Date of Patent: Dec. 13, 2022

(54) HOLE TRANSPORTING MATERIAL, METHOD FOR PREPARING SAME, AND ELECTROLUMINESCENT DEVICE

(71) Applicant: WUHAN CHINA STAR OPTOELECTRONICS SEMICONDUCTOR DISPLAY TECHNOLOGY CO., LTD., Hubei (CN)

(72) Inventor: Jiajia Luo, Wuhan (CN)

(73) Assignee: WUHAN CHINA STAR OPTOELECTRONICS SEMICONDUCTOR DISPLAY TECHNOLOGY CO., LTD., Hubei (CN)

( * ) Notice: Subject to any disclaimer, the term of this patent is extended or adjusted under 35 U.S.C. 154(b) by 292 days.

(21) Appl. No.: 16/629,569

(22) PCT Filed: Oct. 18, 2019

(86) PCT No.: PCT/CN2019/112000
§ 371 (c)(1),
(2) Date: Jan. 9, 2020

(87) PCT Pub. No.: WO2021/000455
PCT Pub. Date: Jan. 7, 2021

(65) Prior Publication Data
US 2021/0043847 A1  Feb. 11, 2021

(30) Foreign Application Priority Data
Jul. 4, 2019  (CN) .......................... 201910602922.2

(51) Int. Cl.
*H01L 51/00* (2006.01)
*C07D 401/14* (2006.01)
(Continued)

(52) U.S. Cl.
CPC ........ *H01L 51/0072* (2013.01); *C07D 401/14* (2013.01); *C07D 403/14* (2013.01);
(Continued)

(58) Field of Classification Search
CPC .............. C07F 15/0033; C07F 15/002; C07F 15/0086; H01L 51/0085; H01L 51/5004;
(Continued)

(56) References Cited

U.S. PATENT DOCUMENTS

2014/0114063 A1* 4/2014 Itoi .................... H01L 51/0059
544/347
2015/0295186 A1  10/2015 Parham et al.

FOREIGN PATENT DOCUMENTS

CN  106467469 A  3/2017
CN  108440424 A  8/2018
(Continued)

OTHER PUBLICATIONS

PCT International Search Report for International Application No. PCT/CN2019/112000, dated Mar. 26, 2020, 6pp.
(Continued)

*Primary Examiner* — Marcos D. Pizarro
*Assistant Examiner* — Quinton A Brasfield
(74) *Attorney, Agent, or Firm* — PV IP PC; Wei Te Chung; Ude Lu (57) ABSTRACT

The present disclosure provides a hole transporting material, a method for preparing the same, and an electroluminescent device. The hole transporting material includes a compound of formula (I):
(Continued)

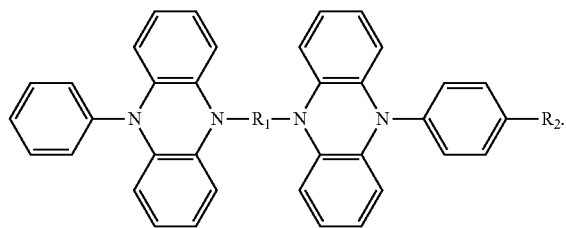

(I)

A series of the hole transport materials with suitable HOMO/LUMO energy levels are synthesized by using bridged dihydrophenazine as a basis and different functional groups. Such materials can be applied to an organic electroluminescent device to improve mobility of a hole transport layer and thus improve luminous efficiency of the organic electroluminescent device.

8 Claims, 1 Drawing Sheet (51) Int. Cl.
C07D 403/14 (2006.01)
C07D 413/14 (2006.01)
H01L 51/50 (2006.01)

(52) U.S. Cl.
CPC ........ *C07D 413/14* (2013.01); *H01L 51/0071* (2013.01); *H01L 51/5056* (2013.01); *H01L 51/5068* (2013.01)

(58) Field of Classification Search
CPC ............. H01L 51/0088; H01L 51/5024; H01L 51/0087; H01L 2251/552; H01L 2251/308; H01L 51/5016; H01L 51/5056–5068
See application file for complete search history.

(56) References Cited

FOREIGN PATENT DOCUMENTS

| CN | 108574051 A | * | 9/2018 | ......... H01L 51/5056 |
| CN | 108863896 A | * | 11/2018 | ......... H01L 51/5056 |
| CN | 108863896 A | | 11/2018 | |

OTHER PUBLICATIONS

PCT Written Opinion for International Application No. PCT/CN2019/112000, dated Mar. 26, 2020, 7pp.
PCT International Preliminary Report on Patenability for International Application No. PCT/CN2019/112000, dated Dec. 28, 2021, 9pp.

* cited by examiner

HOLE TRANSPORTING MATERIAL, METHOD FOR PREPARING SAME, AND ELECTROLUMINESCENT DEVICE

FIELD OF INVENTION

The present disclosure relates to a field of display device technology, and particularly to a hole transporting material, a method for preparing the same, and an electroluminescent device.

BACKGROUND

Organic light-emitting diodes (OLEDs) have attracted attention of many researchers because of their advantages, such as active illumination without backlight, high luminous efficiency, wide viewing angles, fast response times, broader temperature adaptation range, relatively simple production process, low driving voltage, low power consumption, lightness, thin profile, and flexible, and their great application prospects. Luminescent guest materials that play a leading role in OLEDs are critical. Luminescent guest materials used in early OLEDs are fluorescent materials. Since a ratio of singlet and triplet excitons in OLEDs is 1:3, theoretical internal quantum efficiency (IQE) of OLEDs based on fluorescent materials can only reach 25%, which greatly limits applications of fluorescent electroluminescent devices. Heavy metal complex phosphorescent materials can simultaneously use singlet and triplet excitons to achieve 100% IQE due to spin-orbit coupling induced by heavy atoms. However, commonly used heavy metals are precious metals, such as Ir and Pt, and heavy metal complex phosphorescent materials need to be improved in terms of blue light materials.

In a current top-emitting OLED device, a hole transport layer is the thickest layer, and its energy level and hole mobility are always contradictory. There is a need to develop a hole transport material with a matching energy level and high mobility.

SUMMARY OF DISCLOSURE

The present disclosure provides a hole transporting material, a method for preparing the same, and an electroluminescent device, which effectively solve the problem that energy level and hole mobility of a current top-emitting organic light-emitting diode (OLED) device are always contradictory.

In order to achieve the aforementioned purpose, the present disclosure provides a hole transporting material comprising a compound of formula (I):

(I)

$R_1$ and $R_2$ are organic groups.

Furthermore, $R_1$ is selected from:

, and $R_2$ is selected from:

, and

The present disclosure further provides a method for preparing a hole transporting material comprising:

a reaction liquid preparation step: placing a first raw material of formula (II), a second raw material having an $R_2$ group, and a catalyst in a reaction vessel in a strong alkali environment to obtain a reaction liquid;

(II)

a hole transporting material synthesis step: sufficiently reacting the reaction solution at 110-130° C. for 13-25 hours to obtain a mixed solution comprising the hole transporting material;

an extraction step: cooling the mixed solution to room temperature, and extracting the hole transporting material from the mixed solution to obtain a mixture; and a purification step: purifying the extracted mixture obtained in the extraction step to obtain a white powder that is the hole transporting material comprising a compound of formula (I)

(I)

$R_1$ and $R_2$ are organic groups, and X is Cl, Br, or I.

Furthermore, $R_1$ is selected from:

, and

$R_2$ is selected from:

,

,

,

,

,

,

-continued

Furthermore, the second raw material having the $R_2$ group comprises at least one of carbazole, phenoxazine, and N,N-dimethyl acridine. The catalyst is palladium acetate and tri-tert-butylphosphine tetrafluoroborate. The strong alkali environment is made of sodium t-butoxide.

Furthermore, a molar ratio of the first raw material to the second raw material is 1:1 to 1:3.

Furthermore, the reaction liquid preparation step comprises: placing the first raw material, the second raw material, palladium acetate, and tri-tert-butylphosphine tetrafluoroborate in the reaction vessel; passing the reaction vessel through a transition chamber to a glove box containing an argon atmosphere; adding sodium tert-butoxide to the reaction vessel in the glove box; and adding toluene previously dehydrated and deoxygenated to the reaction vessel to obtain the reaction liquid.

Furthermore, the extraction step comprises: pouring the mixed solution into ice water; adding dichloromethane to perform multiple extractions; and combining organic phases to obtain the mixture after multiple extractions. The purification step comprises: purifying the mixture by silica gel column chromatography using a developing agent to obtain the hole transporting material. The developing agent used in silica gel column chromatography is dichloromethane and n-hexane, and a volume ratio of dichloromethane to n-alkane is 1:3.

Furthermore, a molar ratio of the first raw material, the second raw material, palladium acetate, tri-tert-butylphosphine tetrafluoroborate, and sodium tert-butoxide is 1:1.2:0.08:0.24:1.2.

The present disclosure further provides an electroluminescent device comprising: a substrate layer; a hole injection layer disposed on a surface of the substrate layer; a hole transport layer disposed on a surface of the hole injection layer away from the substrate layer; an electron blocking layer disposed on a surface of the hole transport layer away from the hole injection layer; a light emitting layer disposed on a surface of the electron blocking layer away from the hole transport layer; a hole blocking layer disposed on a surface of the light emitting layer away from the electron blocking layer; an electron transport layer disposed on a surface of the hole blocking layer away from the light emitting layer; an electron injection layer disposed on a surface of the electron transport layer away from the hole blocking layer; a half-translucent electrode disposed on a surface of the electron injection layer away from the electron transport layer; and an optical coupling-out layer disposed on a surface of the half-translucent electrode away from the electron injection layer. The hole transport layer is composed of the aforementioned hole transporting material.

In the present disclosure, a series of hole transport materials with suitable HOMO/LUMO energy levels are synthesized by using bridged dihydrophenazine as a basis and different functional groups. Such hole transport materials can improve mobility of a hole transport layer and luminous efficiency of an organic electroluminescent device.

In order to make the above description of the present disclosure more comprehensible, preferred embodiments are described in detail below with reference to accompanying drawings.

DETAILED DESCRIPTION

Technical solutions in embodiments of the present disclosure will be clearly and completely described below with reference to accompanying drawings. The described embodiments are only a part but not all of embodiments of the present disclosure. Based on the embodiments of the present disclosure, all other embodiments obtained by those skilled in the art without any inventive effort should fall within scope of the present invention. The present invention can be embodied in different forms of embodiment, and the scope of the present invention is not limited to the embodiments set forth herein. The following description of the embodiments is not intended to limit the scope of the invention.

The term "embodiment" referred to herein means that a particular feature, structure, or feature described in conjunction with the embodiment may be contained in at least one embodiment of the present disclosure. The term appearing in various places in the specification does not necessarily refer to a same embodiment, nor does it refer to an independent or alternative embodiment that is mutually exclusive with other embodiments. It is expressly and implicitly understood by those skilled in the art that an embodiment described herein may be combined with other embodiments.

The present disclosure provides a hole transporting material comprising a compound of formula (I):

(I)

R₁ and R₂ are organic groups. R₁ is selected from:

R₂ is selected from:

-continued

Figure 1:
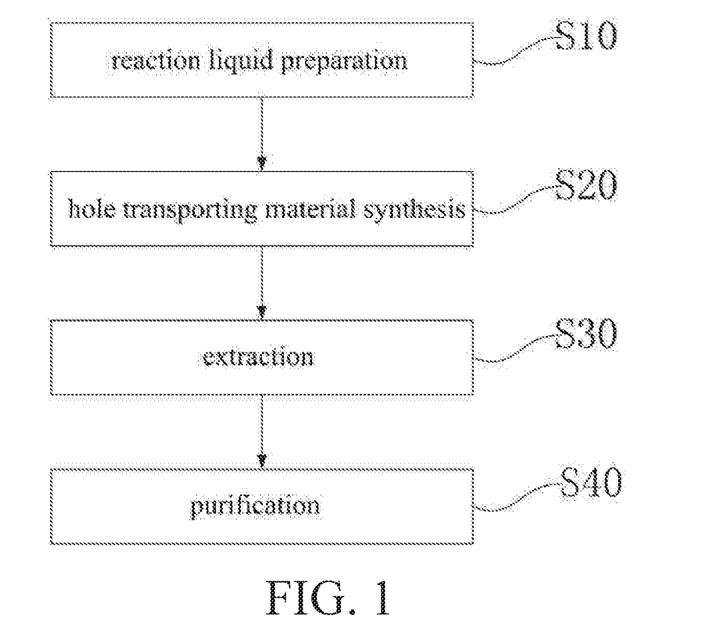
FIG. 1 is a flowchart of a method for preparing the hole transporting material according to an embodiment of the present disclosure.

Please refer to FIG. 1, which is a flowchart of a method for preparing the hole transporting material of the present disclosure. The method for preparing the hole transporting material comprises S10—reaction liquid preparation, S20—hole transporting material synthesis, S30—extraction, and S40—purification.

Step S10—reaction liquid preparation: placing a first raw material of formula (II) and a second raw material having an R₂ group in a reaction vessel in a strong alkali environment at a molar ratio of 1:1 to 1:3, and adding a catalyst to obtain a reaction liquid

(II)

R₁ is selected from:

$R_2$ is selected from:

The second raw material having the $R_2$ group comprises at least one of carbazole, phenoxazine, and N, N-dimethyl acridine. The catalyst is palladium acetate and tri-tert-butylphosphine tetrafluoroborate. The strong alkali environment is made of sodium t-butoxide. Sodium tert-butoxide, a strong base, is widely used in condensation, rearrangement and ring-opening reactions in chemical, pharmaceutical, pesticide, and organic synthesis industries. Because sodium tert-butoxide is highly flammable and reacts violently with water, it is usually stored in a glove box containing an inert atmosphere. Palladium acetate reacts with tri-tert-butylphosphine tetrafluoroborate to produce tri-tert-butylphosphine palladium. Tri-tert-butylphosphine palladium is difficult to preserve due to its high activity, but it is an important catalyst for the method.

The reaction liquid preparation comprises following specific steps: placing the first raw material having the $R_1$ group, the second raw material having the $R_2$ group, palladium acetate, and tri-tert-butylphosphine tetrafluoroborate in the reaction vessel; passing the reaction vessel through a transition chamber to the glove box; and weighing and adding sodium tert-butoxide to the reaction vessel in the glove box. In order to prevent the chemical activity of sodium tert-butoxide and tri-tert-butylphosphine palladium from affecting reaction, it is necessary to change atmosphere inside the glove box to an argon atmosphere in advance, and adding toluene previously dehydrated and deoxygenated to the reaction vessel in the glove box to obtain the reaction liquid.

S20—hole transporting material synthesis: sufficiently reacting the reaction solution at 110-130° C. for 13-25 hours to obtain a mixed solution comprising the hole transporting material. In order to ensure activity and safety of the catalyst and sodium tert-butoxide, this reaction will be carried out in the glove box.

S30—extraction: pouring the mixed solution into ice water; adding dichloromethane to perform multiple extractions; and after multiple extractions, combining organic phases to obtain the mixture.

S40—purification: purifying the mixture by silica gel column chromatography using a developing agent. The mixture is purified to obtain a white powder that is the hole transporting material. The developing agent is dichloromethane and n-hexane, and a volume ratio of dichloromethane to n-alkane is 1:3.

The hole transporting material obtained in the purification step comprises a compound of formula (I):

(I)

X is Cl, Br, or I.

$R_1$ is selected from:

-continued

R$_2$ is selected from:

The method for preparing the hole transporting material is further illustrated by following three specific examples.

Example 1

The disclosure provides a method for preparing a hole transporting material, and a synthetic route is as follows:

The synthesis comprises:

step S10—reaction liquid preparation: adding a first raw material (3.34 g, 5 mmol), carbazole (1.00 g, 6 mmol), palladium acetate (0.09 g, 0.4 mmol), and tri-tert-butylphosphine tetrafluoroborate (0.34 g, 1.2 mmol) to a 250 mL reaction vessel; passing the reaction vessel through a transition chamber to a glove box, wherein the atmosphere inside the glove box is an argon atmosphere; adding sodium tert-butoxide (NaOt-Bu 0.58 g, 6 mmol) to the reaction vessel in a glove box; and adding 100 mL of toluene previously dehydrated and deoxygenated to the reaction vessel to obtain a reaction liquid.

step S20—hole transporting material synthesis: placing the reaction vessel at 120° C. for 24 hours to obtain a mixed solution. This reaction is carried out in the glove box.

step S30—extraction: cooling the mixed solution to room temperature, pouring it into 200 mL of ice water, and extracting it three times with dichloromethane to obtain a mixture.

step S40—purification: combining organic phase of the mixture obtained in the extraction step, purifying the mixture by silica gel column chromatography (dichloromethane: n-alkane, v:v, 1:3) to obtain 3.0 g of white powder that is the hole transporting material. A yield of the hole transporting material produced by this method is 79%, MS (EI) m/z: [M]$^+$: 755.21.

Example 2

The disclosure provides a method for preparing a hole transporting material, and a synthetic route is as follows:

-continued

The synthesis comprises:

step S10—reaction liquid preparation: adding a first raw material (3.34 g, 5 mmol), phenoxazine (1.10 g, 6 mmol), palladium acetate (0.09 g, 0.4 mmol), and tri-tert-butylphosphine tetrafluoroborate (0.34 g, 1.2 mmol) to a 250 mL reaction vessel; passing the reaction vessel through a transition chamber to a glove box, wherein the atmosphere inside the glove box is an argon atmosphere; adding sodium tert-butoxide (NaOt-Bu 0.58 g, 6 mmol) to the reaction vessel in a glove box; and adding 100 mL of toluene previously dehydrated and deoxygenated to the reaction vessel to obtain a reaction liquid.

step S20—hole transporting material synthesis: placing the reaction vessel at 120° C. for 24 hours to obtain a mixed solution. This reaction is carried out in the glove box.

step S30—extraction: cooling the mixed solution to room temperature, pouring it into 200 mL of ice water, and extracting it three times with dichloromethane to obtain a mixture.

step S40—purification: combining organic phase of the mixture obtained in the extraction step, purifying the mixture by silica gel column chromatography (dichloromethane: n-alkane, v:v, 1:3) to obtain 3.1 g of white powder that is the hole transporting material. A yield of the hole transporting material produced by this method is 80%, MS (EI) m/z: [M]+: 771.23.

Example 3

The disclosure provides a method for preparing a hole transporting material, and a synthetic route is as follows:

The synthesis comprises:

step S10—reaction liquid preparation: adding a first raw material (3.34 g, 5 mmol), N, N-dimethyl acridine (1.25 g, 6 mmol), palladium acetate (0.09 g, 0.4 mmol), and tri-tert-butylphosphine tetrafluoroborate (0.34 g, 1.2 mmol) to a 250 mL reaction vessel; passing the reaction vessel through a transition chamber to a glove box, wherein the atmosphere inside the glove box is an argon atmosphere; adding sodium tert-butoxide (NaOt-Bu 0.58 g, 6 mmol) to the reaction vessel in a glove box; and adding 100 mL of toluene previously dehydrated and deoxygenated to the reaction vessel to obtain a reaction liquid.

step S20—hole transporting material synthesis: placing the reaction vessel at 120° C. for 24 hours to obtain a mixed solution. This reaction is carried out in the glove box.

step S30—extraction: cooling the mixed solution to room temperature, pouring it into 200 mL of ice water, and extracting it three times with dichloromethane to obtain a mixture.

step S40—purification: combining organic phase of the mixture obtained in the extraction step, purifying the mixture by silica gel column chromatography (dichloromethane: n-alkane, v:v, 1:3) to obtain 3.3 g of white powder that is the hole transporting material. A yield of the hole transporting material produced by this method is 83%, MS (EI) m/z: [M]+: 797.21.

Theoretical electrochemical energy levels of the hole transporting materials of the three specific examples of the present disclosure are shown in Table 1 below.

TABLE 1

|  | HOMO (eV) | LUMO (eV) |
| --- | --- | --- |
| Example 1 | −5.51 | −2.53 |
| Example 2 | −5.59 | −2.51 |
| Example 3 | −5.61 | −2.55 |

The hole transporting material obtained in Example 1 has a theoretical HOMO of −5.51 eV and a theoretical LUMO of −2.53 eV.

The hole transporting material obtained in Example 2 has a theoretical HOMO of −5.59 eV and a theoretical LUMO of −2.51 eV.

The hole transporting material obtained in Example 3 has a theoretical HOMO of −5.61 eV and a theoretical LUMO of −2.55 eV.

It can be seen that the hole transporting materials synthesized by this method have stable and reliable performance.

Figure 2:
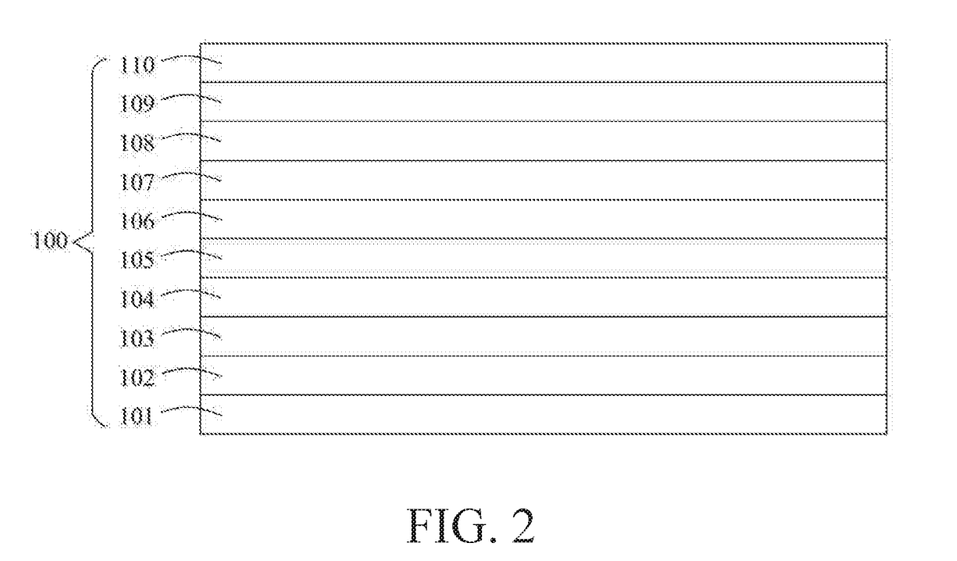
FIG. 2 is a schematic structural diagram of an electroluminescent device according to an embodiment of the present disclosure.

The present disclosure further provides an electroluminescent device 100 as shown in FIG. 3. The electroluminescent device 100 comprises a substrate layer 101, a hole injection layer 102, a hole transport layer 103, an electron blocking layer 104, a light emitting layer 105, a hole blocking layer 106, an electron transport layer 107, an electron injection layer 108, a half-translucent electrode 109, and an optical coupling-out layer 110. The hole transport layer is composed of one of the hole transporting materials disclosed in the above examples.

The hole injection layer disposed on a surface of the substrate layer. The hole transport layer disposed on a surface of the hole injection layer away from the substrate layer. The electron blocking layer disposed on a surface of the hole transport layer away from the hole injection layer. The light emitting layer disposed on a surface of the electron blocking layer away from the hole transport layer. The hole blocking layer disposed on a surface of the light emitting layer away from the electron blocking layer. The electron transport layer disposed on a surface of the hole blocking layer away from the light emitting layer. The electron injection layer disposed on a surface of the electron transport layer away from the hole blocking layer. The half-translucent electrode disposed on a surface of the electron injection layer away from the electron transport layer. The optical coupling-out layer disposed on a surface of the half-translucent electrode away from the electron injection layer.

When the hole transport layer 103 employs one of the materials of the above three specific examples, performance data of the electroluminescent device 100 is as shown in Table 2 below.

TABLE 2

| Hole transport layer | Maximum current efficiency (cd/A) | (CIEx, CIEy) | Maximum external quantum efficiency (%) |
|---|---|---|---|
| Compound of Example 1 | 45.6 | (0.683, 0.290) | 38.6% |
| Compound of Example 2 | 45.8 | (0.685, 0.293) | 39.0% |
| Compound of Example 3 | 46.1 | (0.686, 0.295) | 39.9% |

When the electroluminescent device 100 is fabricated using the hole transporting material prepared in Example 1, the device 100 has a maximum current efficiency of 45.6 cd/A, a color coordinate (CIEx, CIEy) of (0.683, 0.290), and a maximum external quantum efficiency of 38.6%.

When the electroluminescent device 100 is fabricated using the hole transporting material prepared in Example 2, the device 100 has a maximum current efficiency of 45.8 cd/A, a color coordinate (CIEx, CIEy) of (0.685, 0.293), and a maximum external quantum efficiency of 39%.

When the electroluminescent device 100 is fabricated using the hole transporting material prepared in Example 3, the device 100 has a maximum current efficiency of 46.1 cd/A, a color coordinate (CIEx, CIEy) of (0.686, 0.295), and a maximum external quantum efficiency of 39.9%.

In summary, a hole transporting layer of an organic light-emitting diode (OLED) device of the present disclosure is composed of the hole transporting material disclosed in the present disclosure, which can effectively solve the problem that energy level and hole mobility of a current top-emitting organic light-emitting diode (OLED) device are always contradictory. In the present disclosure, a series of hole transport materials with suitable HOMO/LUMO energy levels are synthesized by using bridged dihydrophenazine as a basis and different functional groups. Such hole transport materials can improve mobility of a hole transport layer and luminous efficiency of an organic electroluminescent device.

A hole transporting material, a method for preparing the same, and an electroluminescent device provided by the examples of the present disclosure are described in detail above. Principles and implementations of the present application are described herein with specific examples. The above description of the examples is merely for assisting in understanding solutions of the present application and its core idea. Those skilled in the art can make changes in the specific examples and application scopes according to the idea of the present application. In summary, the content of this specification should not be construed as limiting the present invention.

What is claimed is:

1. A hole transporting material, comprising a compound of formula (I):

wherein $R_1$ is selected from:

, and

-continued and
$R_2$ is selected from:

2. An electroluminescent device, comprising:
a substrate layer;
a hole injection layer disposed on a surface of the substrate layer;
a hole transport layer disposed on a surface of the hole injection layer away from the substrate layer;
an electron blocking layer disposed on a surface of the hole transport layer away from the hole injection layer;
a light emitting layer disposed on a surface of the electron blocking layer away from the hole transport layer;
a hole blocking layer disposed on a surface of the light emitting layer away from the electron blocking layer;
an electron transport layer disposed on a surface of the hole blocking layer away from the light emitting layer;
an electron injection layer disposed on a surface of the electron transport layer away from the hole blocking layer;
a half-translucent electrode disposed on a surface of the electron injection layer away from the electron transport layer; and
an optical coupling-out layer disposed on a surface of the half-translucent electrode away from the electron injection layer;
wherein the hole transport layer is composed of the hole transporting material according to claim 1.

3. A method for preparing a hole transporting material, comprising:
a reaction liquid preparation step: placing a first raw material of formula (II), a second raw material having an R2 group, and a catalyst in a reaction vessel in a strong alkali environment to obtain a reaction liquid;

(II)

a hole transporting material synthesis step: sufficiently reacting the reaction solution at 110-130° C. for 13-25 hours to obtain a mixed solution comprising the hole transporting material;
an extraction step: cooling the mixed solution to room temperature, and extracting the hole transporting material from the mixed solution to obtain a mixture; and
a purification step: purifying the mixture obtained in the extraction step to obtain a white powder that is the hole transporting material comprising a compound of formula (I);

(I)

wherein

X is Cl, Br, or I;

R₁ is selected from:

and

R₂ is selected from:

4. The method for preparing the hole transporting material according to claim 3, wherein
the second raw material having the R2 group comprises at least one of carbazole, phenoxazine, and N, N-dimethyl acridine;
the catalyst is palladium acetate and tri-tert-butylphosphine tetrafluoroborate; and
the strong alkali environment is made of sodium t-butoxide.

5. The method for preparing the hole transporting material according to claim 3, wherein a molar ratio of the first raw material to the second raw material is 1:1 to 1:3.

6. The method for preparing the hole transporting material according to claim 4, wherein the reaction liquid preparation step comprises:
placing the first raw material, the second raw material, palladium acetate, and tri-tert-butylphosphine tetrafluoroborate in the reaction vessel;
passing the reaction vessel through a transition chamber to a glove box containing an argon atmosphere;
adding sodium tert-butoxide to the reaction vessel in the glove box; and
adding toluene previously dehydrated and deoxygenated to the reaction vessel to obtain the reaction liquid.

7. The method for preparing the hole transporting material according to claim 3, wherein
the extraction step comprises:
pouring the mixed solution into ice water;
adding dichloromethane to perform multiple extractions; and
after multiple extractions, combining organic phases to obtain the mixture; and the purification step comprises:
purifying the mixture by silica gel column chromatography using a developing agent to obtain the hole transporting material;
wherein the developing agent used in silica gel column chromatography is dichloromethane and n-hexane, and a volume ratio of dichloromethane to n-alkane is 1:3.

8. The method for preparing the hole transporting material according to claim 4, wherein a molar ratio of the first raw material, the second raw material, palladium acetate, tri-tert-butylphosphine tetrafluoroborate, and sodium tert-butoxide is 1:1.2:0.08:0.24:1.2.

* * * * *